(12) United States Patent
Kim et al.

(10) Patent No.: US 7,906,694 B2
(45) Date of Patent: Mar. 15, 2011

(54) METHOD OF PREPARING MONO-IODO BENZENE THROUGH TRANSIODINATION

(75) Inventors: Han-Seok Kim, Yongin (KR); Jong-In Lee, Seongnam (KR); Il-Hoon Cha, Anyang (KR); Yong-Ki Park, Daejeon (KR); Won-Choon Choi, Daejeon (KR); Bu-Sub Song, Daejeon (KR)

(73) Assignee: SK Chemicals Co., Ltd., Suwon (KR)

( * ) Notice: Subject to any disclaimer, the term of this patent is extended or adjusted under 35 U.S.C. 154(b) by 16 days.

(21) Appl. No.: 12/519,894

(22) PCT Filed: Nov. 23, 2007

(86) PCT No.: PCT/KR2007/005959
§ 371 (c)(1),
(2), (4) Date: Jun. 18, 2009

(87) PCT Pub. No.: WO2008/082082
PCT Pub. Date: Jul. 10, 2008

(65) Prior Publication Data
US 2010/0094067 A1    Apr. 15, 2010

(30) Foreign Application Priority Data

Dec. 29, 2006    (KR) .................. 10-2006-0137806

(51) Int. Cl.
*C07C 17/00* (2006.01)
(52) U.S. Cl. ...................................... 570/206; 570/202
(58) Field of Classification Search .................. 570/202, 570/206
See application file for complete search history.

(56) References Cited

U.S. PATENT DOCUMENTS

| 4,792,641 A | 12/1988 | Rule et al. |
| 4,806,698 A | 2/1989 | Rule et al. |
| 4,808,759 A | 2/1989 | Paparatto |
| 4,822,929 A | 4/1989 | Paparatto |
| 5,157,170 A | 10/1992 | Mais et al. |

FOREIGN PATENT DOCUMENTS

| EP | 0 181 790 | 5/1986 |
| EP | 0 183 579 | 6/1986 |
| JP | 57-077631 | 5/1982 |
| JP | 58-077830 | 5/1983 |
| JP | 59-219241 | 12/1984 |
| SU | 453392 | 1/1975 |

OTHER PUBLICATIONS

Uemura et al., Aromatic Bromination and Iodination with Mixtures of Antimony (V) Chloride and Halogens, Bulletin of the Chemical Society of Japan, vol. 47 (1), 147-150, Jan. 1974, pp. 147-150.
Datta et al, Holgenation. XV. Direct Iodination of Hydrocarbons by Means of Iodine and Nitric Acid., The Chemical Laboratory of Presidency College, Dec. 26, 1916, pp. 435-441.
International Search Report and Written Opinion dated Mar. 5, 2008. PCT/KR2007/005959.

*Primary Examiner* — Jafar Parsa
(74) *Attorney, Agent, or Firm* — Gifford, Krass, Sprinkle, Anderson & Citkowski, P.C.

(57) ABSTRACT

The present invention relates to a method of preparing mono-iodo benzene with a transiodination reaction, and more preferably a method of preparing mono-iodo benzene including a step of performing transiodination of a reactant including benzene and at least a multi-iodo benzene selected from the group consisting of di-iodo benzene and tri-iodo benzene with an HY or HBeta type of zeolite having a Si/Al molar ratio of 10 to 100 as a catalyst. The method of the present invention has an advantage that iodine is recovered from by-products including m-di-iodo benzene, o-di-iodo benzene, and tri-iodo benzene obtained in the process of preparing p-di-iodo benzene, thereby resulting in minimizing the loss of iodine.

6 Claims, 4 Drawing Sheets

METHOD OF PREPARING MONO-IODO BENZENE THROUGH TRANSIODINATION

CROSS-REFERENCE TO RELATED APPLICATIONS

This application is the U.S. national phase of PCT/KR2007/005959 filed Nov. 23, 2007, which claims priority of Korean Patent Application No. 10-2006-0137806 filed Dec. 29, 2006.

BACKGROUND OF THE INVENTION (a) Field of the Invention

The present invention relates to a method of preparing mono-iodo benzene with a transiodination reaction, and more specifically to a method of preparing mono-iodo benzene by using multi-iodo benzene of a by-product produced in oxy-iodination.

(b) Description of the Related Art

An oxy-iodination reaction that synthesizes iodobenzene starting from benzene and iodine is carried out slowly, and thus is usually in liquid phase in the presence of an oxidative agent such as nitric acid, acetic acid, hydrogen peroxide, or silver sulfide.

The oxy-iodination reaction has been described in JP S58-077830 A, U.S.S.R. 453392, the Journal of the American Chemical Society, Vol. 39, page 437, 1917,etc.

In the oxy-iodination reaction, other oxidizing agents including iodic acid ($HIO_3$), sulfur trioxide ($SO_3$), and hydrogen peroxide ($H_2O_2$) have also been suggested, but none of these have proven to be more efficient than nitric acid.

The iodination reaction using metal halogenides as catalysts instead of an oxidizing agent is disclosed in the Bulletin of Chemical Society of Japan, Vol. 47, page 147, 1974. In the JP S57-077631 A, benzene is directly iodinated in gaseous phase by using 13X-type zeolite.

JP S59-219241 A suggested that an iodobenzene compound was produced from benzene by using a very acidic zeolite catalyst having a molar ratio of silicon to aluminum (Si/Al) of greater than 10 with oxy-iodination in an oxygen atmosphere.

EP0181790B and EP0183579B disclose methods for the synthesis of iodobenzene by oxidative iodination in a gaseous phase starting from benzene, iodine, and oxygen in the presence of air or other oxygen-containing gas with a zeolite catalyst. EP0181790B discloses zeolite catalysts of ZSM-5 type and ZSM-11 type that have been exchanged with divalent or trivalent cations prior to use. EP 0183579B suggested X-type or Y-type zeolite in non-acidic form to prevent inactivation of the catalyst, and the X-type or Y-type zeolite has to be used in a form in which it is exchanged with monovalent, divalent, or trivalent cations, and in particular, an alkaline metal or rare earth metal. In the methods of EP0181790B and EP0183579B, mono-iodo benzene (MIB) is produced with selectivity of higher than 90%, and only distinctly minor amounts of di-iodo benzene (DIB) compounds are produced as by-products.

As noted above, in the conventional methods, an iodinated aromatic compound is synthesized selectively with oxy-iodination. As shown in Reaction schemes 1 to 3, however, the oxy-iodination produces various iodinated aromatic compounds and undesired iodinated aromatic compounds as by-products.

$2C_6H_6+I_2+O_2 \rightarrow 2C_6H_5I+H_2O$     [Reaction Scheme 1]

$2C_6H_5I+I_2+O_2 \rightarrow 2C_6H_4I_2+H_2O$     [Reaction Scheme 2]

$2C_6H_5I_2+I_2+O_2 \rightarrow 2C_6H_3I_3+H_2O$     [Reaction Scheme 3]

Because iodine is very expensive, the by-products of iodinated aromatic compounds are produced disadvantageously. Thus, iodine-containing by-products except MIB and p-DIB are required to convert to MIB and p-DIB with transiodination.

The transiodination method of iodinated aromatic compounds has been disclosed in U.S. Pat. Nos. 4,792,641, 4,806, 698, 4,808,759 and 4,822,929. U.S. Pat. No. 4,792,641 discloses a method of transiodination of aromatic compounds, particularly DIB in a gaseous phase at 275~500° C. with a non-acidic zeolite catalyst of an X type that is exchanged with an alkaline metal or alkaline earth metal prior to use. U.S. Pat. No. 4,806,698 disclose a method of transiodination of aromatic compounds, particularly iodonaphthalene, in a liquid phase at 180~250° C. with acidic zeolite of an X-type, Y-type, or L-type. The methods have a disadvantage of serious inactivation of the catalyst, because iodonaphthalene is only used without a diluting agent such as benzene naphthalene.

EP 4808759B discloses a method of transiodination of polyiodobenzene, particularly DIB, at 250~450° C. in the presence of benzene and oxygen with zeolites of an X or Y type exchanged with an alkaline metal or rare earth metal. EP 4822929B discloses a method of transiodination of polyiodobenzene, particularly DIB, with pentacyl zeolite exchanged with cations of a group II metal, a group III metal, or a group IV metal.

In most of the conventional methods, zeolites of X, Y, L, or ZSM-5 types in non-acidic form are used. In addition, the reaction conditions such as reaction temperature and reactant composition are different depending on the kinds of aromatic compounds such as benzene and naphthalene, but this has not been studied sufficiently. In particular, a method of increasing the selectivity of product and the stability of catalyst needs to be further studied.

SUMMARY OF THE INVENTION

To resolve the problems of the conventional method, an object of the present invention is to provide a method of preparing mono-iodo benzene (MIB) through transiodination from multi-iodo benzenes such as m-di-iodo benzene (m-DIB), o-di-iodo benzene (o-DIB), tri-iodo benzene (TIB), and the like, which are by-products of oxy-iodination reaction.

BRIEF DESCRIPTION OF THE DRAWINGS

For a more complete understanding of the present invention, and the advantages thereof, reference is now made to the following description in conjunction with the accompanying drawings, in which.

DETAILED DESCRIPTION OF THE PREFERRED EMBODIMENTS

These and other objects of the invention will be more fully understood from the following description of the invention, the referenced drawings attached hereto, and the claims appended hereto.

To achieve the object, the present invention provides a method of preparing a mono-iodo benzene that is prepared from a reaction product including benzene and at least a multi-iodo benzene selected from the group consisting of di-iodo benzene and tri-iodo benzene with transiodination using an HY or HBeta type of zeolite having a Si/Al molar ratio of 5 to 100 as a catalyst.

The present invention will be further explained in more detail.

The present inventors carried out the transiodination under various reaction conditions and thus obtained MIB selectively without lowering the activity of a catalyst with the addition of benzene to multi-iodo benzene, and using HY-type zeolite, and more preferably an acidic HY-type zeolite catalyst having a Si/Al molar ratio of 5 to 100.

Furthermore, while the transiodination is carried out for 10 days or more, the catalyst begins to be inactivated. The inactivated catalyst can be recovered by calcining it in the presence of oxygen or air.

Figure 1:
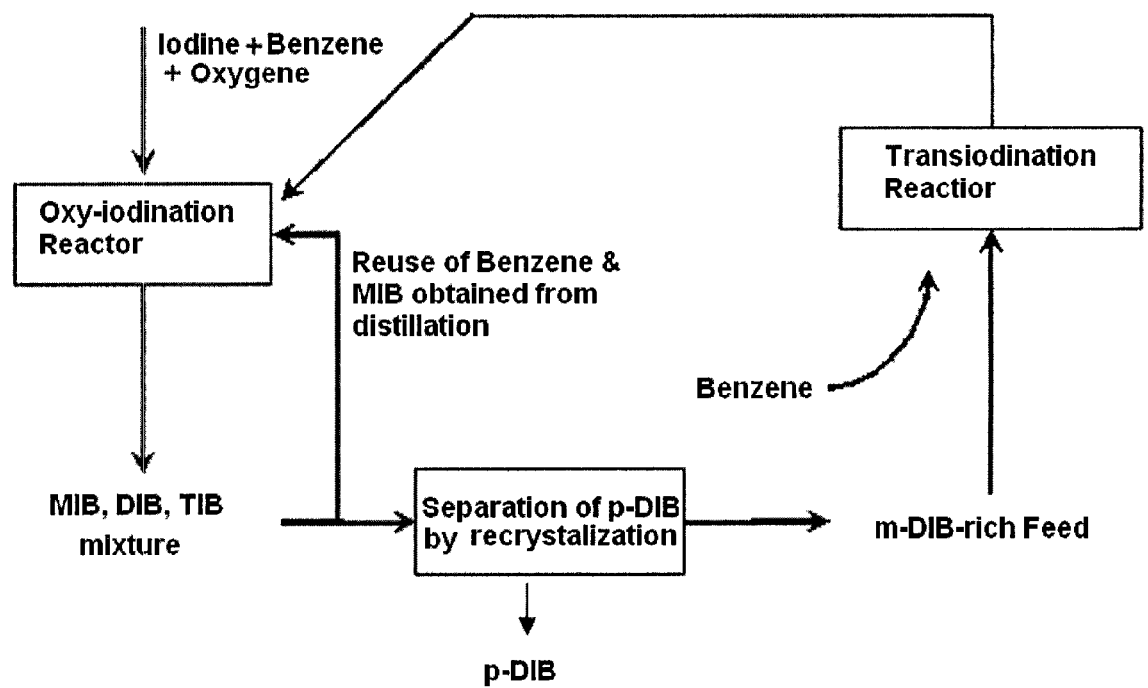
FIG. 1 is a schematic drawing showing the transiodination process.

The transiodination means the intramolecular movement (isomerization) or intermolecular movement of iodine atoms contained in the molecule, and can be used for production of MIB and p-DIB. MIB and p-DIB are used as a starting material for preparing highly expensive engineering plastics such as poly phenyl sulfide (PPS).

p-DIB, which is a main starting material for preparing PPS, is efficiently produced from benzene and iodine by combining oxy-iodination and transiodination, which can include the process illustrated in FIG. 1.

More specifically, oxy-iodination of benzene and iodine produces p-DIB, and by-products of which benzene and MIB are distilled and transferred to an oxy-iodination reactor, and of which multi-iodo benzenes such as m-DIB, o-DIB, TIB, etc. are crystallized, separated, and transferred to a transiodination reactor to be converted to MIB. MIB is transferred to an oxy-iodination reactor.

Even though the by-products such as m-DIB, o-DIB, TIB, etc. are produced in such process of the present invention, they are recovered and reused efficiently without loss of iodine.

The key aspect of the present invention is the combination of oxy-iodination and transiodination, and particularly the transiodination of m-DIB, o-DIB, and TIB, which are by-products of oxy-iodination. Loss of iodoaromatic compounds in two reactions causes serious problems economically. Thus, to minimize the loss of iodine, studies on oxy-iodination and transiodination reactions and suitable catalysts are required. In particular, the reactant composition, reaction temperature, Si/Al molar ratio of zeolite catalyst, acidity, and the like are considered as factors affecting the selectivity to MIB and catalyst inactivation in the transiodination.

In an embodiment, an HY-type zeolite catalyst having a Si/Al molar ratio of 5 to 100 is used as the catalyst, and a reactant including benzene and at least a multi-iodo benzene selected from the group consisting of di-iodo benzene and tri-iodo benzene are required for transiodination.

The catalyst that is useful for the present invention is a solid acid catalyst such as zeolite with certain acidity and pore structure. The highly acidity of a zeolite catalyst is generated by ion-exchanging the catalyst with ammonium ions and then calcining it to be converted to hydrogen ions. Exemplary zeolite catalysts are X type, Y type, L type, ZSM-5 type, Mordenite, and the like. To control the acidity and pore size, the catalyst can be ion-exchanged or supported with transition metals, rare earth metals, alkaline metals, alkaline earth metals, and the like. In an embodiment of the present invention, a $H^+$ type of zeolite exchanged with hydrogen ions is more preferable than a $Na^+$ type of zeolite exchanged with non-acidic alkaline metal ions. The Si/Al molar ratio of the zeolite catalyst ranges from 5 to 100, and more preferable from 10 to 15.

In addition, the multi-iodo benzene is a remnant obtained by removing mono-iodo benzene and p-di-iodo benzene from a reaction product of oxy-iodination of benzene, iodine, and oxygen, and more preferably is at least one selected from the group consisting of m-di-iodo benzene, o-di-iodo benzene, and tri-iodo benzene.

In the transiodination, benzene is added to the multi-iodo benzene, thereby improving the selectivity to MIB and preventing the inactivation of the catalyst. In particular, the added benzene plays an important role in reducing the inactivation speed of the catalyst. As the amount of added benzene is increased, the catalyst inactivation decreases and the selectivity to MIB increases.

Thus, to increase the selectivity to MIB and prevent the catalyst inactivation, a molar ratio of benzene to multi-iodo benzene is equal to or more than 2:1, more preferably 3:1 or more, and most preferably 25:1 or more for sufficiently providing iodine. The addition of benzene to the reaction product plays a key role in stably obtaining MIB from multi-iodo benzene.

In the transiodination, other reaction conditions except for the catalyst and reactant are not particularly limited, but the reaction temperature is more important than other reaction conditions.

When the reaction temperature is excessively low, initial selectivity to MIB increases due to the decreased side-reaction, but the catalyst activity decreases rapidly due to coke deposited in the catalyst. If the reaction temperature is excessively high, the temperature needs to be optimized because of the decreased selectivity to MIB. Thus, the transiodination is performed at 120 to 250° C. and more preferably at 160 to 200° C. to maintain the selectivity to MIB and the catalyst activity.

In addition, like the reaction temperature, the reaction pressure is important for catalyst inactivation. The reaction pressure is preferably maintained at a prescribed pressure or lower. That is, the reaction pressure is preferably maintained to be lower than the pressure at which benzene contained in the reactant exists in a gaseous phase. If the reaction pressure is higher, it is possible for the catalyst to be inactivated quickly. Thus, the reaction pressure is maintained at about 1 atm at the reaction temperature of 120 to 250° C., and is preferable maintained at 10 atm or less at which benzene can be liquefied to prevent the catalyst inactivation.

However, if the transiodination is performed for a long time, the reaction activity and the selectivity to MIB can declines sharply after a specific time. It is suggested that such problem is caused by deposition of materials that inhibit the catalyst activity in the catalyst. It is very difficult to prevent the materials from being deposited. Thus, the catalyst can be recycled and reused to remove the deposited materials.

In an embodiment of the present invention, the catalyst can be recycled by calcination. Preferably, the inactivated catalyst is calcined by heating at 400 to 650° C. in an oxygen or air atmosphere, thereby resulting in an active catalyst that is useful for transiodination. The calcined catalyst has the same activity as a fresh catalyst.

The present invention is further explained in more detail with reference to the following examples. These examples, however, should not be interpreted as limiting the scope of the present invention in any manner.

The transiodination in the examples was carried out at the following reaction conditions.

To prevent channeling of reaction product and loss of reaction pressure, the catalyst was prepared by pressing the powdery catalyst and granulating it to a granule size of 20 to 40 mesh.

The reactor was a stainless steel tubular type of reactor with a diameter ¾", and 2 g of catalyst granules were poured and reacted.

The catalyst was treated by flowing dry air at a speed of 100 ml/min at 500° C. for 3 hours before use.

The input speed of reactant was 2 mL/h while flowing nitrogen as a carrier gas at a flow speed of 20 mL/min.

Benzene and iodobenzene compound ("feed") were mixed in the reactant at a weight ratio of 3:7, 5:5, 7:3, or 9:1, as shown in Table 1.

The feed used for the examples was a mixture of benzene and a remnant obtained by removing MIB and p-DIB from a reaction product of oxy-iodination.

As shown in Table 1, the feed included m-DIB and o-DIB as main components, and MIB, p-DIB, and TIB as minor components.

The components in the feed were analyzed by a gas chromotograph (GC) equipped with an AT-35 column and an FID detector.

TABLE 1

|  | Reactant 1 | Reactant 2 | Reactant 3 | Reactant 4 |
|---|---|---|---|---|
| Benzene/Feed (weight ratio) | 7:3 | 5:5 | 3:7 | 1:9 |
| Benzene/Feed (molar ratio) | 16.5:1 | 3.3:1 | 1.5:1 | 0.6:1 |
| Benzene (mol %) | 94.29 | 76.50 | 59.68 | 37.71 |
| MIB (mol %) | 0.26 | 0.62 | 0.90 | 1.36 |
| p-DIB (mol %) | 0.67 | 2.82 | 4.44 | 2.55 |
| m-DIB (mol %) | 3.19 | 12.86 | 21.64 | 37.33 |
| o-DIB (mol %) | 1.05 | 4.38 | 7.18 | 10.91 |
| TIB (mol %) | 0.54 | 2.82 | 6.16 | 10.12 |

EXAMPLES 1 TO 4, AND COMPARATIVE EXAMPLES 1 TO 4

2 g of a catalyst described in Table 2 and Reactant 1 of Table 1 were input at a feed speed of 2 ml/hr and reacted at 180° C., 1 atm. The reaction products after the passage of reaction time were collected, and the components were analyzed and the results are shown in Table 2.

TABLE 2

|  | Catalyst | Time (h) | MIB | p-DIB | m-DIB | o-DIB | TIB |
|---|---|---|---|---|---|---|---|
| Example 1 | HY (5)* | 2 | 41.9 | 0.0 | 50.1 | 7.0 | 1.0 |
|  |  | 4 | 29.8 | 0.0 | 56.2 | 10.6 | 3.3 |
|  |  | 6 | 26.5 | 0.0 | 59.1 | 11.3 | 3.1 |
|  |  | 8 | 19.3 | 0.0 | 50.7 | 10.4 | 19.6 |
| Example 2 | HY (12)* | 2 | 82.2 | 5.1 | 10.6 | 2.1 | 0.0 |
|  |  | 4 | 74.7 | 7.3 | 15.0 | 3.0 | 0.2 |
|  |  | 6 | 72.4 | 7.7 | 16.0 | 3.1 | 0.8 |
|  |  | 8 | 68.1 | 8.8 | 18.5 | 3.6 | 1.0 |
| Example 3 | HY (80)* | 2 | 83.8 | 3.9 | 10.7 | 1.6 | 0.0 |
|  |  | 4 | 70.8 | 4.9 | 22.0 | 2.1 | 0.1 |
|  |  | 6 | 66.8 | 5.4 | 25.0 | 2.3 | 0.5 |
|  |  | 8 | 64.9 | 5.0 | 26.7 | 2.2 | 1.3 |
| Example 4 | HBeta (25)* | 2 | 78.7 | 4.8 | 13.8 | 2.3 | 0.3 |
|  |  | 4 | 69.6 | 5.9 | 20.3 | 3.5 | 0.7 |
|  |  | 6 | 66.0 | 6.6 | 23.2 | 3.4 | 0.9 |
|  |  | 8 | 66.4 | 6.0 | 23.2 | 3.3 | 1.2 |
| Comparative example 1 | HZSM-5 (25)* | 2 | 37.2 | 0.0 | 47.8 | 14.1 | 0.9 |
|  |  | 4 | 38.1 | 0.0 | 46.3 | 13.9 | 1.8 |
|  |  | 8 | 38.7 | 0.3 | 45.2 | 14.1 | 1.8 |
| Comparative example 2 | Na-ZSM-5 (25)* | 2 | 15.0 | 22.6 | 53.3 | 8.2 | 0.9 |
|  |  | 4 | 8.1 | 30.8 | 44.4 | 15.8 | 0.8 |
|  |  | 6 | 5.9 | 27.5 | 48.0 | 17.7 | 0.9 |
| Comparative example 3 | HX | 2 | 7.5 | 13.4 | 60.8 | 17.2 | 1.1 |
|  |  | 4 | 3.3 | 11.6 | 57.3 | 18.4 | 9.4 |
|  |  | 6 | 2.5 | 66.5 | 66.5 | 18.2 | 12.8 |
|  |  | 8 | 2.6 | 66.1 | 66.1 | 17.9 | 13.4 |
| Comparative example 4 | Alumina | 2 | 5.6 | 12.4 | 58.0 | 18.3 | 5.7 |
|  |  | 4 | 4.5 | 12.5 | 61.4 | 19.3 | 2.3 |
|  |  | 6 | 2.8 | 10.0 | 57.6 | 18.1 | 11.5 |
|  |  | 8 | 2.5 | 0.0 | 68.8 | 18.6 | 10.1 |

*(numerical value) represents Si/Al molar ratio.

As seen from Table 1, HY-type zeolite and HBeta-type zeolite showed superior activity and selectivity to MIB to HZSM-5, HX, and HL type zeolite.

As the Si/Al molar ratio of HY zeolite catalyst increased, the selectivity to MIB increased and showed maximum catalytic activity at a Si/Al molar ratio of 10 or higher with less loss of catalyst activity with the passage of reaction time. HZSM-5, alumina, and an X type of zeolite showed very low catalytic activity.

EXAMPLES 5 AND 6, AND COMPARATIVE EXAMPLE 5

To investigate the effect of transiodination temperature, these examples were evaluated substantially the same as Example 2 except that the transiodination temperatures were 120° C. (Example 5), 180° C. (Example 6), and 100° C. (Comparative Example 5). The selectivities to MIB with the passage of reaction time were measured and are shown in FIG. 2.

Figure 2:
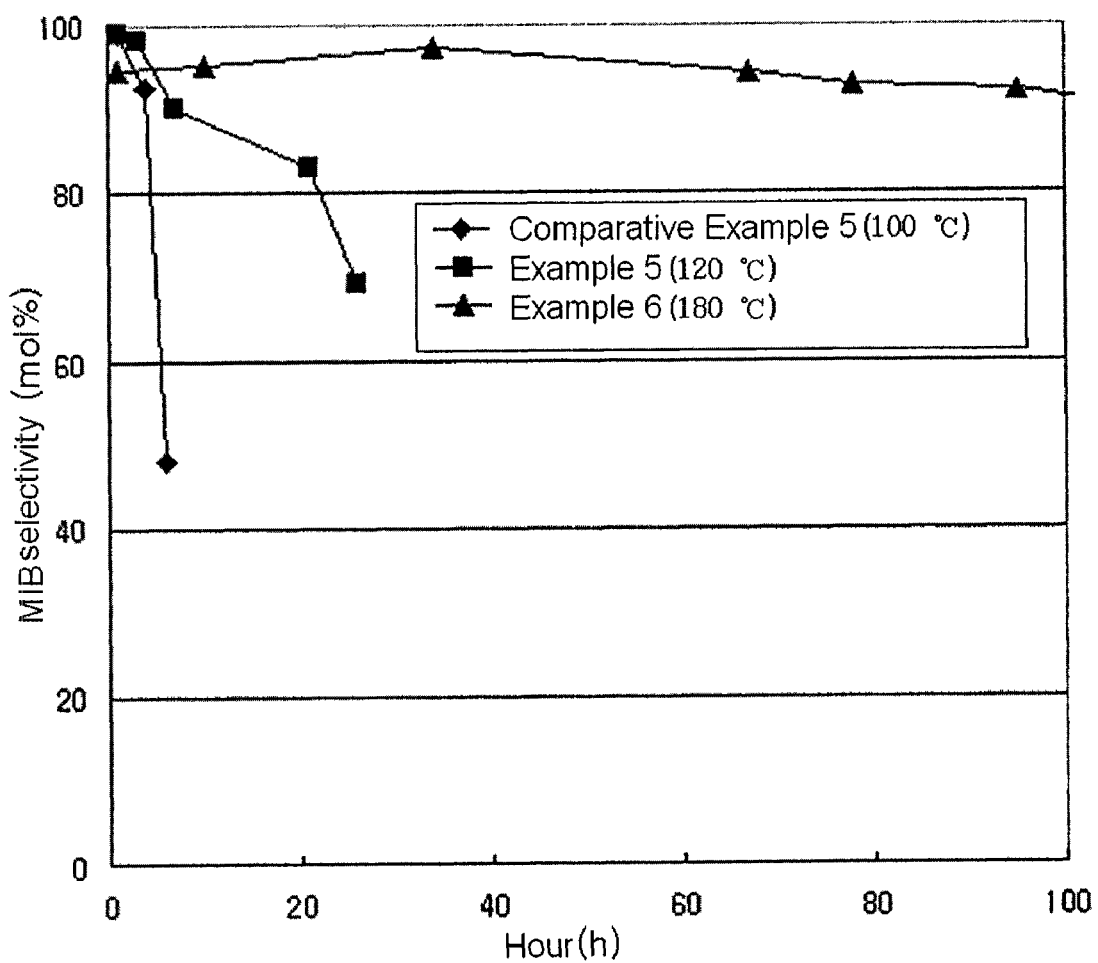
FIG. 2 is a graph of MIB selectivity with the passage of transiodination time in the method of Examples 5 and 6, and Comparative Example 5.

As shown in FIG. 2, when the reaction temperature was lower the selectivity to MIB was higher, but the catalyst activity decreased rapidly due to coke deposited in the catalyst. That is, when the temperature was lower than 120° C. (Comparative Example 5), the catalyst activity decreased rapidly with the passage of the reaction time. On the other hand, when the temperature was at 120° C. or higher (Examples 5), the initial selectivity to MIB began to decrease slowly. When the reaction was performed for a long time at 180° C. or higher (Example 6), the catalyst activity did not decrease.

EXAMPLES 7 AND 8, AND COMPARATIVE EXAMPLES 6 AND 7

To investigate the effect of feed composition, these examples were evaluated substantially the same as the Example 2 except that the feeds were Reactant 1 (Example 7), Reactant 2 (Example 8), Reactant 3 (Comparative Example 6), and Reactant 4 (Comparative Example 7). The selectivity to MIB with the passage of reaction time were measured and shown in FIG. 3.

Figure 3:
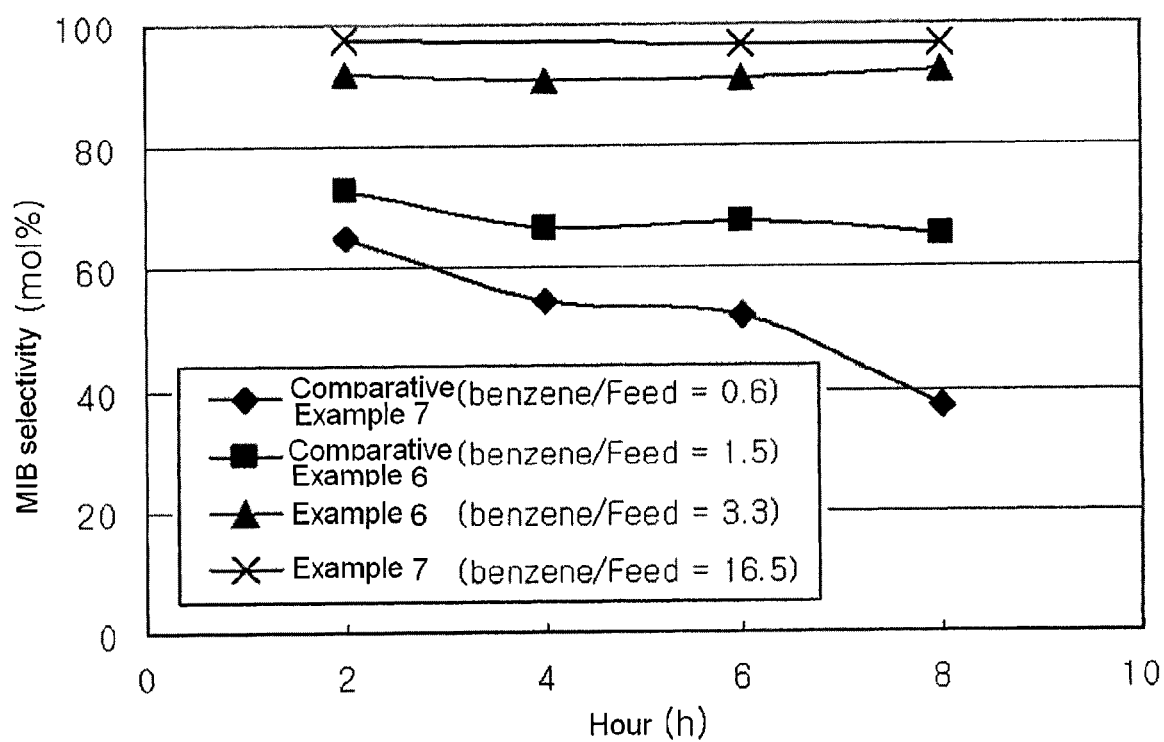
FIG. 3 is a graph of MIB selectivity with the passage of transiodination time in methods of Examples 7 and 8, and Comparative Examples 6 and 7.

As seen from FIG. 3, the reactants of Examples 7 and 8 with molar ratios of benzene/Feed of 2:1 or higher showed superior selectivity to MIB with no catalyst inactivation. However, the reactants of Comparative Examples 6 and 7 with molar ratios of benzene/Feed of lower than 2:1 showed low selectivity to MIB and a decrease of catalyst activity with the passage of reaction time.

EXAMPLE 9

The transiodination in Example 7 was performed until the catalyst was inactivated. Then, the inactivated catalyst was recycled by calcining at 485° C. for 12 hours in an air atmosphere. The transiodination was carried out with recycled catalyst under the same conditions as of Example 7.

Figure 4:
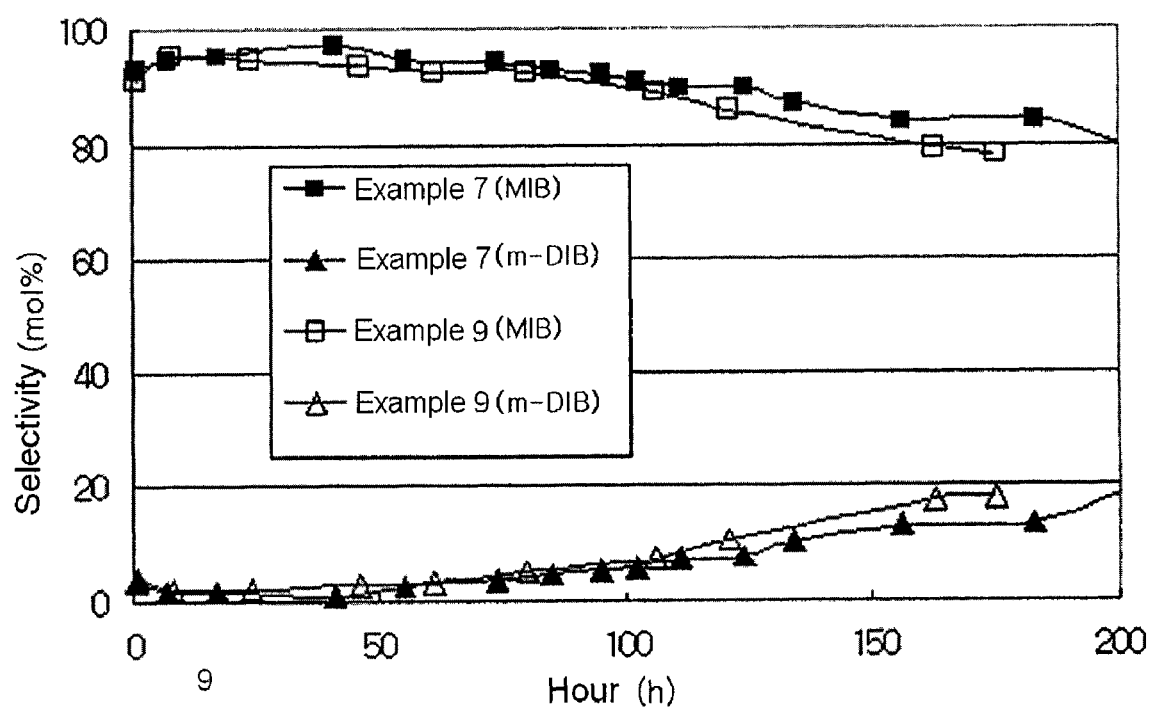
FIG. 4 is a graph of MIB selectivity with the passage of transiodination time in methods of Example 7 using a fresh catalyst and Example 9 using a recycled catalyst.

The selectivities to MIB in Example 7 using a fresh catalyst and Example 9 using the recycled catalyst are shown in FIG. 4.

As shown in FIG. 4, the selectivity to MIB in Example 7 was maintained consistently at 90% or more for up to 80 hours of reaction time, but decreased slowly after 80 hours, which was similar to the selectivity of Example 9 using the recycled catalyst.

These examples confirmed that the recycling of the catalyst caused the catalyst activity to be recovered. The recovery efficiency of the catalyst was very high, and thus the catalyst can be reused several times without detrimental effects.

The preparation method of the present invention is advantageous in recovering iodine from m-di-iodo benzene, o-di-iodo benzene, and tri-iodo benzene, which are obtained in general production of p-di-iodo benzene as by-products, while minimizing the loss of iodine.

What is claimed is:

1. A method of preparing a mono-iodo benzene comprising a step of transiodinating a reactant including benzene and at least a multi-iodo benzene selected from the group consisting of di-iodo benzene and tri-iodo benzene with HY-type or HBeta-type zeolite having a molar ratio of silicon to aluminum (Si/Al) of 5 to 100 as a catalyst, wherein the reactant comprises benzene and multi-iodo benzene at a molar ratio of 2:1 to 25:1 and the transiodinating step is carried out at 120 to 250° C.

2. The method of preparing a mono-iodo benzene according to claim 1, wherein the multi-iodo benzene is a remnant obtained by removing mono-iodo benzene and p-di-iodo benzene from a reaction product of oxy-iodination of benzene, iodine, and oxygen.

3. The method of preparing a mono-iodo benzene according to claim 1, wherein the multi-iodo benzene is at least one selected from the group consisting of m-di-iodo benzene, o-di-iodo benzene, and tri-iodo benzene.

4. The method of preparing a mono-iodo benzene according to claim 1, wherein the transiodinating step is carried out at 1 to 10 atm.

5. The method of preparing a mono-iodo benzene according to claim 1, wherein the transiodinating step is carried out by using acidic HY-type or HBeta-type zeolite.

6. The method of prepaing a mono-iodo benzene according to claim 1, wherein the method of preparing a mono-iodo benzene further comprises a step of reusing a recycled catalyst that is obtained by calcining the catalyst at 400 to 650° C. in a oxygen or air atmosphere.

* * * * *